United States Patent [19]

Finnieston et al.

[11] Patent Number: 4,553,535
[45] Date of Patent: Nov. 19, 1985

[54] THIGH BRACE

[76] Inventors: Alan Finnieston, 2380 W. 82nd St., Hialeah, Fla. 33016; Joseph B. Zagorski, 355 Marquesa Dr., Coral Gables, Fla. 33156

[21] Appl. No.: 530,005

[22] Filed: Sep. 7, 1983

[51] Int. Cl.[4] .............................................. A61F 3/00
[52] U.S. Cl. .................................................... 128/88
[58] Field of Search ................ 128/80 F, 80 C, 80 R, 128/87 R, 88, 80 H, DIG. 15

[56] References Cited

U.S. PATENT DOCUMENTS

| | | | |
|---|---|---|---|
| 3,827,431 | 8/1974 | Pecorella | 128/80 F |
| 4,353,361 | 10/1982 | Foster | 128/80 |
| 4,393,866 | 7/1983 | Finnieston | 128/87 R |
| 4,407,276 | 10/1983 | Bledsoe | 128/80 C |

Primary Examiner—C. Fred Rosenbaum
Assistant Examiner—Christa K. Scott
Attorney, Agent, or Firm—Larson and Taylor

[57] ABSTRACT

A thigh brace for maintaining broken bone segments in the proper healing orientation by protecting and reinforcing the surfaces of the upper leg between the hip and knee is disclosed. The thigh brace includes an elongate generally U-shaped interior member which extends around the laterally interior surface of the upper leg and which is flexible. The thigh brace also includes an elongate, generally C-shaped exterior member which extends around the laterally exterior surface of the upper leg and which is similarly flexible. The longitudinal side edges of the exterior member are disposed in overlapping relationship with the longitudinal side edges of the interior member so that the exterior member and interior member encase the upper leg and provide increased lateral support to hold the broken bone segments in the proper healing orientation and protect against valgus or varus movement of the broken bone segments. The thigh brace also includes a keeper for holding the members in mating relationship and a retaining device for retaining the members in the desired location on the upper leg. Preferably, the retaining device is a tibia brace secured to the lower leg and connected to the thigh brace. Conveniently, the connection is a pair of pivoted struts having two axes pivots. The struts are attached to the thigh brace and recesses provided in the members.

8 Claims, 7 Drawing Figures 4,553,535

THIGH BRACE

FIELD OF THE INVENTION

The present invention relates generally to a brace for maintaining broken bone segments in a proper healing orientation, and more particularly to an upper leg brace which holds broken bone fragments in a proper healing orientation and helps prevent the bone segments from moving into a valgus or varus orientation.

BACKGROUND OF THE INVENTION

Numerous devices have been disclosed in the prior art for maintaining broken bone segments of the upper leg in a fixed, healing orientation. The most common type of device is the well-known plaster cast. Various semi-rigid braces have also been disclosed in the prior art for holding broken bone segments in a proper healing orientation.

Due to the constant deforming forces acting on the fragments of a fractured femur, there is a tendency for the upper bone fragment to move to a valgus or outward orientation and for the lower bone fragment to move to a varus or inward orientation. A rigid plaster cast assures that no deforming forces move the bone segments in a broken femur. However, flexible or semi-flexible braces can allow some such movement.

SUMMARY OF THE INVENTION

In accordance with the present invention, a thigh brace is provided for maintaining the broken bone segments of a femur in a proper healing orientation. In addition, the thigh brace of the present invention provides an increased laterally directed force on either side of the bone segments to assure that no movement into valgus or varus by the bone segments is allowed. The thigh brace includes an elongate, generally U-shaped interior member having a base and sidewalls extending around the laterally interior surface of the upper leg. The interior member is made of a semi-rigid material with the sidewalls capable of being flexed. An elongate, generally C-shaped exterior member is also provided having a base and sidewalls extending around the laterally exterior surface of the upper leg. The exterior member is similarly made of a semi-rigid material with sidewalls capable of being flexed. The longitudinal side edges of the exterior member are disposed in overlapping relationship with the longitudinal side edges of the interior member so that the interior and exterior members encase the upper leg with the inner surfaces of the interior and exterior members in contact with the surfaces of the upper leg. A keeper means is also provided for stabilizing the members in mating relationship to one another and a retaining means is provided for retaining the members in a desired location on the upper leg. By positioning the bases of the members along the lateral sides of the upper leg, the bases provide the pressing force which holds the bone segments against a valgus or varus orientation.

In a preferred embodiment of the present invention, the retaining means includes a tibia brace which is secured about the lower leg and which is connected to the thigh brace so that the tibia brace and thigh brace move as a unit along the length of the leg. Preferably, a pair of pivoted struts are attached to respective lateral sides of the thigh brace and tibia brace to connect the two. As the pivot axis of the knee varies according to the orientation of the upper and lower leg, a two axes pivot for the connecting struts is also preferably provided.

The tibia brace includes an elongate, generally U-shaped posterior member and an elongate, generally C-shaped anterior member. The anterior and posterior members encase the lower leg to hold the tibia brace relatively immovably in place. A heel rest is preferably attached to the posterior member as well.

The pivoted struts are preferably made of a rigid plastics material. The struts are conveniently attached to the inside surface of respective interior and exterior members in a recess provided in the bases thereof.

In the preferred embodiment, the keeper means includes fastener means such as straps for releasably fastening the interior and exterior members together. The straps extend around a substantial portion of the periphery of the thigh brace so that the thigh brace exerts a force around the entire periphery of the upper leg. For a better fit, the exterior and interior members are tapered along their length to conform with the tapering of the upper leg.

Other features and advantages of the present invention are stated in or appear from a detailed description of a presently preferred embodiment of the invention found hereinbelow..

DETAILED DESCRIPTION OF THE PREFERRED EMBODIMENT

Figure 1:
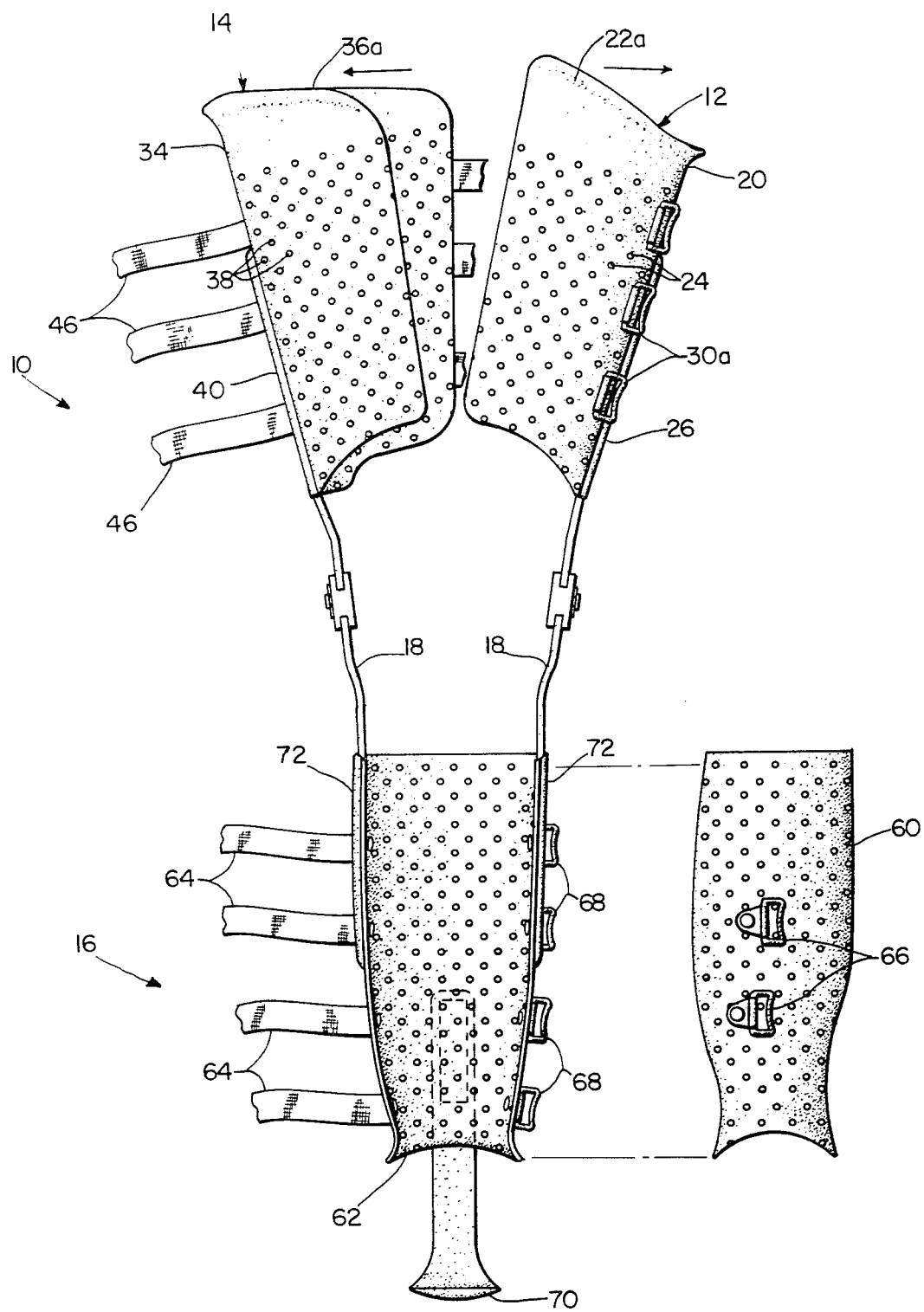
FIG. 1 is a front plan view of the thigh brace according to the present invention with the interior and exterior members moved laterally apart for clarity.

With reference now to the drawings in which like numerals represent like elements throughout the several views, a presently preferred embodiment of a thigh brace 10 for the right leg of a user is depicted in FIG. 1. Thigh brace 10 includes an interior member 12 and an exterior member 14. Interior member 12 and exterior member 14 are connected to a tibia brace 16 by a pair of pivoted struts 18. Tibia brace 16 is the subject of applicant's prior U.S. Pat. No. 4,393,866, which patent is herein incorporated by reference.

Figure 2:
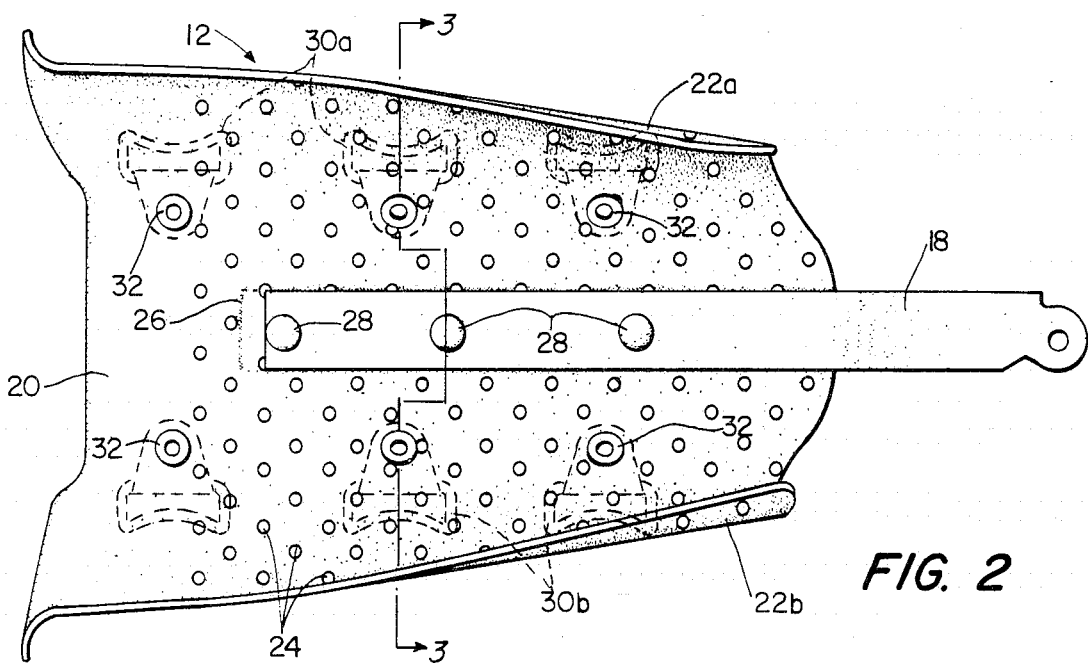
FIG. 2 is a right side view of the interior member depicted in FIG. 1.
Figure 3:
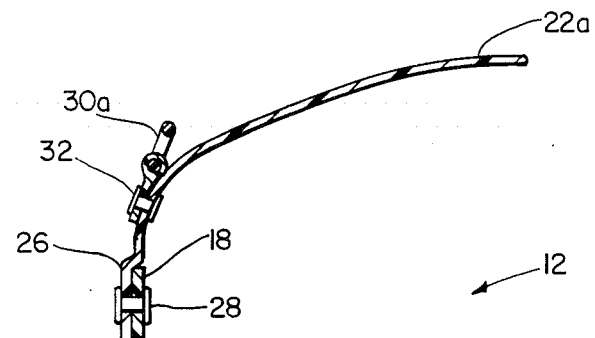
FIG. 3 is a cross-sectional top view of the interior member depicted in FIG. 2 taken along the line 3—3.

With additional reference to FIGS. 2 and 3, it can be seen that interior member 12 has a generally U-shaped cross-section and includes a base 20 and side walls 22a and 22b. Interior member 12 is made of a semi-rigid plastics material so that side walls 22a and 22b are somewhat flexible relative to base 20.

Both base 20 and side walls 22a and 22b are provided with a plurality of holes 24. Base 20 also includes a recess 26 along a portion of the longitudinal length thereof in which the upper end of strut 18 is received. As shown, strut 18 is attached to base 20 in recess 26 by rivets 28. Recess 26 allows the interior surface of base 20 to be relatively smoothly shaped. Located on either side of recess 26 on the outer surface of base 20 are a plurality of hook members 30a and 30b. Hook members 30a and 30b are attached to base 20 by rivets 32. As shown, interior member 12 tapers slightly to follow the tapering of the thigh of the user.

Figure 4:
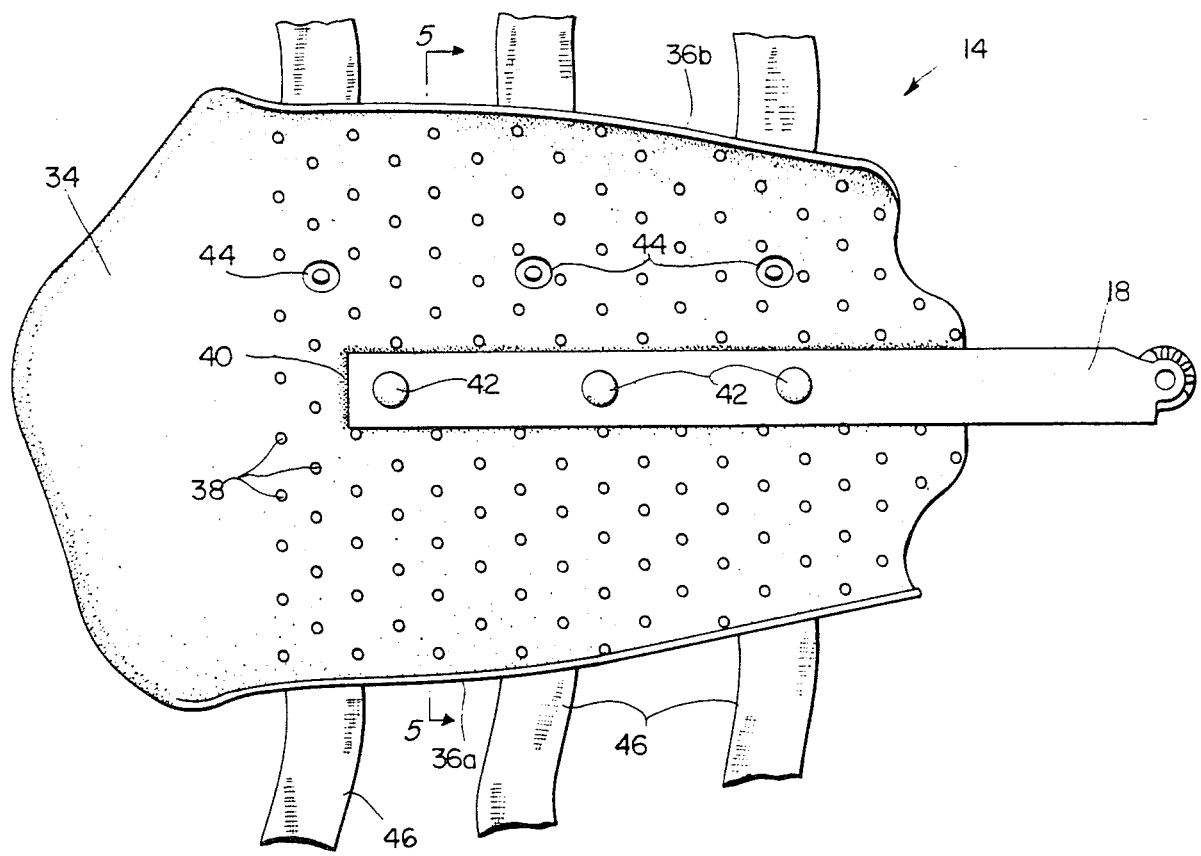
FIG. 4 is a left side view of the exterior member depicted in FIG. 1.
Figure 5:
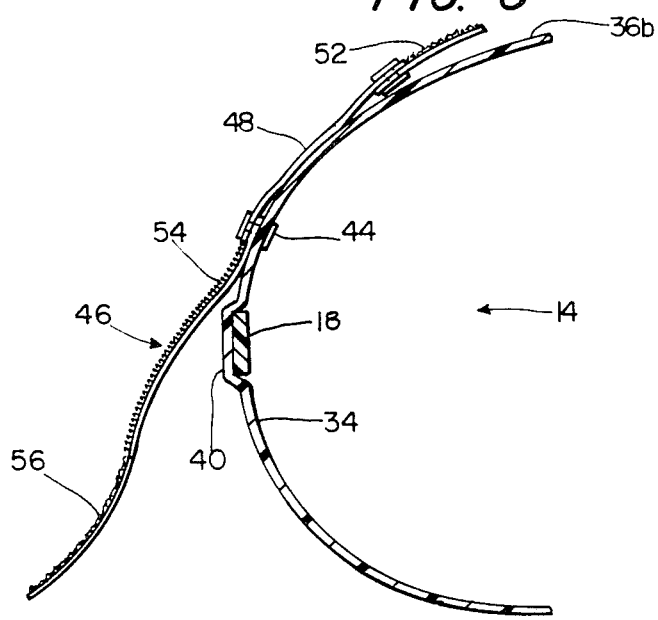
FIG. 5 is a cross-sectional top view of the exterior member depicted in FIG. 4 taken along the line 5—5.

With additional reference now to FIGS. 4 and 5, it can be seen that exterior member 14 is generally C-shaped in cross-section. Exterior member 14 includes a base 34 and side walls 36a and 36b. As with interior member 12, exterior member 14 is similarly made of a semi-rigid plastics material and includes a number of holes 38 therein.

In a manner similar to interior member 12, exterior member 14 also includes a recess 40 along the longitudinal length of base 34. The other strut 18 is located in recess 40 and is attached to exterior member 14 by rivets 42. Recess 40 allows the interior surface of exterior member 14 to maintain a relatively smooth interior surface on base 34. Attached to exterior member 14 by suitable rivets 44 are three straps 46.

Figure 6:
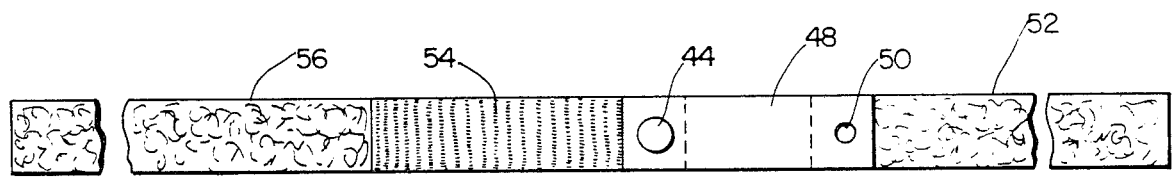
FIG. 6 is a plan view of a strap used to hold the interior and exterior members together.

A strap 46 is depicted in greater detail in FIG. 6. Strap 46 includes Velcro type fastening sections allowing strap 46 to be attached to itself as will be explained subsequently. Strap 46 includes a plastic section 48 having a permanent hook member extending therefrom. Attached to plastic section 48 on one side by a rivet 50 is a loop section 52. On the other side of plastic section 48, a releasable hook section 54 is provided. Releasable hook section 54 is attached to plastic section 48 by a rivet 44 which also attaches strap 46 to exterior member 14. Finally, another loop section 56 is attached at the end of releasable hook section 54. Loop section 56 can be releasably attached to releasably hook section 54 as will be explained subsequently.

As mentioned above, tibia brace 16 is the subject of applicant's prior patent. Tibia brace 16 includes a generally C-shaped anterior member 60 and a generally U-shaped posterior member 62. Anterior member 60 is matingly received inside of posterior member 62 so that the longitudinal side edges of anterior member 60 are disposed within the longitudinal side edges of posterior member 62 so that anterior member 60 and posterior member 62 encase the lower leg of the user. The bases of anterior member 60 and posterior member 62 and portions of the side walls are in contact with the surface of the lower leg and held relatively movably in place by use of straps 64. As explained in the above-identified patent, straps 64 are attached to posterior member 62 and pass through hook member 66 on anterior member 60 and hook member 68 on posterior member 62. Finally, straps 64 double back on themselves over hook members 66. Straps 64 include a loop section at one end and a hook section at the other so that the ends of straps 64 can be attached to each other to securely hold anterior member 60 and posterior member 62 on the lower leg. Tibia brace 16 also includes a heel rest 70. Preferably, heel rest 70 is adjustably secured to posterior member 62 by a Velcro loop section attached to heel rest 70 and a plastic section of permanent hooks attached to the rear area of posterior member 62.

In order to attach struts 18 to tibia brace 16, posterior member 62 is provided with recesses 72 on either lateral side. Struts 18 are then suitably attached by rivets to posterior member 62.

Figure 7:
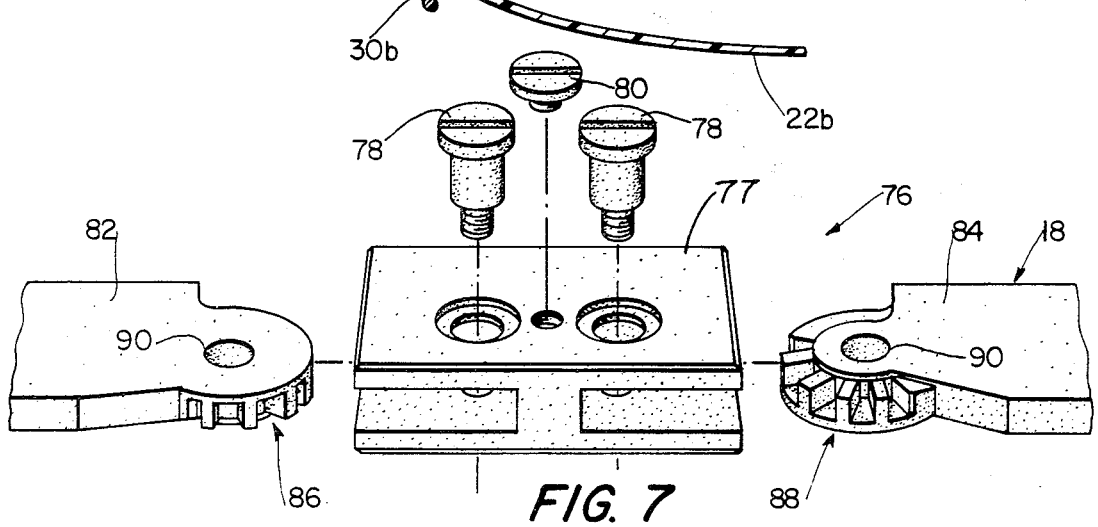
FIG. 7 is an exploded side view of the strut pivot depicted in FIG. 1.

As shown in greater detail in FIG. 7, pivoted struts 18 are provided with a two axis pivot 76. Such a two axis pivot is manufactured by American Prosthetics Supply Inc. of Ames, Iowa. Pivot 76 includes a base 77. Base 78 includes two plates which are spaced from one another and in which pivot pins 78 are threadly received at one end. A lock screw 80 is also threadably received in the upper plate to prevent further rotation of pivot pins 78.

As shown, the ends 82 and 84 of strut 18 which are joined at pivot 76 have mating toothed sections 86 and 88. An aperture 90 is provided in the center of toothed sections 86 and 88 in which respective pivot pins 78 are located when pivot 76 is assembled. Because of toothed sections 86 and 88, ends 82 and 84 move in unison with similar but opposite angular movements whenever pivoting takes place in pivot 76.

In operation, thigh brace 10 functions in the following manner. Initially, the broken femur is set by the physician. Then, the leg is positioned in thigh brace 10. In order to do this, anterior member 60 is removed and interior member 12 and exterior member 14 separated laterally as shown in FIG. 1. Normally, struts 18 hold interior member 12 resiliently against exterior member 14. However, with struts 18 made of a hard but resilient plastic, interior member 12 and exterior member 14 can be separated from one another a sufficient distance to allow the upper leg of the user to be positioned therebetween.

Once the leg of the user is positioned in thigh brace 10 anterior member 60 is positioned over the lower leg and straps 64 fed through hook member 66 and hook member 68. Making sure that the heel of the user is positioned on heel rest 70, straps 64 are pulled tight and doubled over one another to secure the Velcro fastenings at each end. The securing of tibia brace 16 locates interior member 12 and exterior member 14 along the upper leg.

Next, interior member 12 and exterior member 14 are pushed together with the longitudinal side edges of exterior member 14 being disposed in overlapping relationship with the longitudinal side edges of interior member 12. Next, straps 34 are passed through hook members 30a and 30b. It should be noted that loop section 52 is passed through hook members 30b while loop section 56 is passed through hook members 30a. Loop sections 52 and 56 are then pulled tight so that interior member 12 and exterior member 14 encase the upper leg with the inner surfaces of interior member 12 and exterior member 14 in positive contact with the surface of the upper leg. Loop section 52 is then permanently attached to plastic section 48 while loop section 56 is releasably attached to releasable hook section 54. Straps 46 extend around a substantial portion of thigh brace 10 and provide pressure around substantially the whole periphery of thigh brace 10.

It should be noted that interior member 12 and exterior member 14 produce inwardly directed forces on the upper leg of the user. These inwardly directed forces are caused by the location of base 20 and base 34 on opposite lateral sides of the upper leg. In this manner, the tendency of the broken bone segments to move into a valgus or varus orientation is acted against and the broken bone segments are positively held in a desired healing orientation.

It should also be noted that the use of tibia brace 16 acts to positively hold thigh brace 10 in the desired position on the upper leg so that thigh brace 10 continues to hold the upper leg in desired healing orientation. In addition, pivot 76 allows the lower leg of the user to be moved relative to the upper leg while still maintaining thigh brace 10 in the proper location. The use of a dual axes pivot 76 also accommodates the changing axis location of the knee joint to add to the comfort of the user and the positive location of the thigh brace relative to the upper leg.

It should further be noted that the use of struts 18 made of a plastics material provides a hygenic material for connecting thigh brace 10 and tibia brace 16. In addition, such a plastics material is relatively light weight compared to the use of a metal for struts 18.

By permanently attaching loop section 52 to plastic section 48, on the posterior side of thigh brace 10, it is possible for the user to undo loop section 56 from releasable hook section 54 and to remove the upper leg from thigh brace 10 if desired for short periods of time. Because loop section 52 is permanently attached to plastic section 48, it is thereby easy to reattach thigh brace 10 to the upper leg by simply pulling loop section 56 to desired tension without having to worry about the mating relationship of interior member 12 and exterior member 14 which has been maintained by the attachment of loop section 52 to plastic section 48.

It is also contemplated in rare cases that where a fracture of the femur and tibia bones occurs, thigh brace 10 and tibia brace 16 can be used together to hold both bones in a proper healing orientation.

Although the present invention has been described with respect to a thigh brace 10 which is usable on the right leg of the user, it should be appreciated that a complementary shaped thigh brace for the left leg is also possible.

Thus, while the present invention has been described with respect to an exemplary embodiment thereof, it will be understood by those of ordinary skill in the art that variations and modifications can be effected within the scope and spirit of the invention.

We claim:

1. A thigh brace for maintaining broken bone segments in the proper healing orientation by protecting and reinforcing the surfaces of the upper leg between the hip and knee, said brace comprising:
    an elongage, generally U-shaped interior member having a base and sidewalls extending around the laterally interior surface of the upper leg, said interior member being made of semi-rigid material with said sidewalls capable of being flexed;
    an elongate, generally C-shaped exterior member having a base and sidewalls extending around the laterally exterior surface of the upper leg, said exterior member being made of semi-rigid material with said sidewalls capable of being flexed, the longitudinal side edges of said exterior member being disposed in overlapping relationship with the longitudinal side edges of said interior member whereby said interior and exterior members encase the upper leg with the inner surfaces of said interior and exterior members in contact with the surface of the upper leg;
    a keeper means for stabilizing said members in mating relation to one another;
    a retaining means for retaining said members in the desired location on the upper leg,
    said retaining means including a tibia brace which is secured about the lower leg and a connecting means for connecting said tibia brace to said thigh brace such that said tibia brace and said thigh brace move as a unit along the longitudinal length of the leg, said connecting means including a pair of pivoted struts attached to respective lateral sides of said thigh brace and said tibia brace;
    the pivot of each of said pivoted struts comprising a two-axis pivot to accomodate the changing center axis of the knee as the knee flexes.

2. A thigh brace as claimed in claim 1 wherein said tibia brace includes an elongate, generally U-shaped posterior member having a base and sidewalls extending around the posterior surface of the lower leg and an elongate, generally C-shaped anterior member having a base and sidewalls extending around the anterior surface of the lower leg, the longitudinal side edges of said anterior member being disposed in overlapping relationship with the longitudinal side edges of the posterior member whereby said anterior and posterior members encase the lower leg with the inner surfaces of said anterior and posterior members being in contact with the surface of the lower leg and held relatively immovably in place.

3. A thigh brace as claimed in claim 2 wherein said tibia brace further includes a heel rest attached to said posterior member.

4. A thigh brace as claimed in claim 1 wherein said pivoted struts are made of a rigid plastics material.

5. A thigh brace as claimed in claim 4 wherein said pivoted struts are attached to the inside surface of respective said interior and exterior members, said interior and exterior members having a recess in said bases on which said struts are located whereby the relatively smooth U-shape and C-shape, respectively, of the inside surfaces of said interior and exterior members are maintained.

6. A thigh brace as claimed in claim 1 wherein said keeper means includes fastener means for releasably fastening said interior and exterior members together.

7. A thigh brace as claimed in claim 6 wherein said fastener means includes straps extending around a substantial portion of the periphery of said thigh brace.

8. A thigh brace as claimed in claim 1 wherein said members are tapered along the length of said members to conform with the tapering of the upper leg.

* * * * *